United States Patent
Huang et al.

(10) Patent No.: US 9,758,818 B2
(45) Date of Patent: Sep. 12, 2017

(54) POLYMERASE CHAIN REACTION-BASED METHOD AND PRIMER SET FOR DETECTING EPIDERMAL GROWTH FACTOR RECEPTOR MUTATION

(76) Inventors: Jr-Kai Huang, Taiwan (CN); Chi-Kuan Chen, Taiwan (CN); Tao-Yeuan Wang, Taiwan (CN)

( * ) Notice: Subject to any disclaimer, the term of this patent is extended or adjusted under 35 U.S.C. 154(b) by 578 days.

(21) Appl. No.: 14/370,000

(22) PCT Filed: Dec. 30, 2011

(86) PCT No.: PCT/CN2011/085015
§ 371 (c)(1),
(2), (4) Date: Sep. 10, 2014

(87) PCT Pub. No.: WO2013/097173
PCT Pub. Date: Jul. 4, 2013

(65) Prior Publication Data
US 2015/0037795 A1     Feb. 5, 2015

(51) Int. Cl.
*C12P 19/34*     (2006.01)
*C12Q 1/68*     (2006.01)

(52) U.S. Cl.
CPC ........... *C12Q 1/6858* (2013.01); *C12Q 1/686* (2013.01); *C12Q 1/6848* (2013.01)

(58) Field of Classification Search
USPC ............................................ 435/6.12, 91.2
See application file for complete search history.

(56) References Cited

U.S. PATENT DOCUMENTS

2013/0149695 A1* 6/2013 Lee ..................... C12Q 1/6858
435/5

OTHER PUBLICATIONS

Behn et al., Thromb. Haemost. 79, 773-777 (1998).*

* cited by examiner

*Primary Examiner* — Kenneth Horlick

(57) ABSTRACT

Disclosed herein is a polymerase chain reaction (PCR)-based method for detecting an insertion/deletion variant, as compared with a reference sequence, in a selected region of a target gene in a sample. The target gene has a template strand and a coding strand complementary to the template strand. The method uses a primer set that includes a blocking primer, and a forward primer. The blocking primer and the forward primer are partially overlapping and have different melting temperatures, and the 3'-end of the blocking primer is modified to prevent the extension of the blocking primer during the PCR. Accordingly, under specific PCR conditions, the presence of the PCR product is indicative of the presence of an insertion/deletion mutation in the selected region, and the absence of the PCR product is indicative of the absence of an insertion/deletion mutation in the selected region.

4 Claims, 2 Drawing Sheets

FORWARD PRIMER

5'- AATTCCCGTCGCTATCAA -3'

BLOCKING PRIMER

5'- CGCTATCAAGGAATTAAGAGAAGCAACATCTCC🚫 -3'

TARGET GENE (REFERENCE SEQUENCE)

5'-TAAAATTCCCGTCGCTATCAAGGAATTAAGAGAAGCAACATCTCCGAA-3'
3'-ATTTTAAGGGCAGCGATAGTTCCTTAATTCTCTTCGTTGTAGAGGCTT-5'

TARGET GENE (VARIANT SEQUENCE)

5'-TAAAATTCCCGTCGCTATCAAGGAATAACATCTCCGAA-3'
3'-ATTTTAAGGGCAGCGATAGTTCCTTATTGTAGAGGCTT-5'

HYBRIDIZATION WITH REFERENCE SEQUENCE

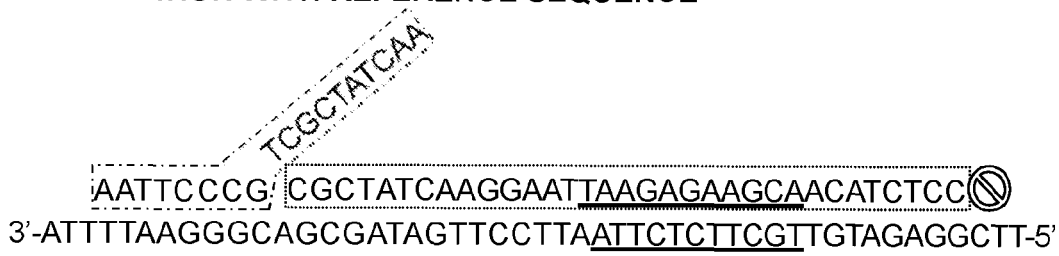
3'-ATTTTAAGGGCAGCGATAGTTCCTTAATTCTCTTCGTTGTAGAGGCTT-5'

HYBRIDIZATION WITH VARIANT SEQUENCE

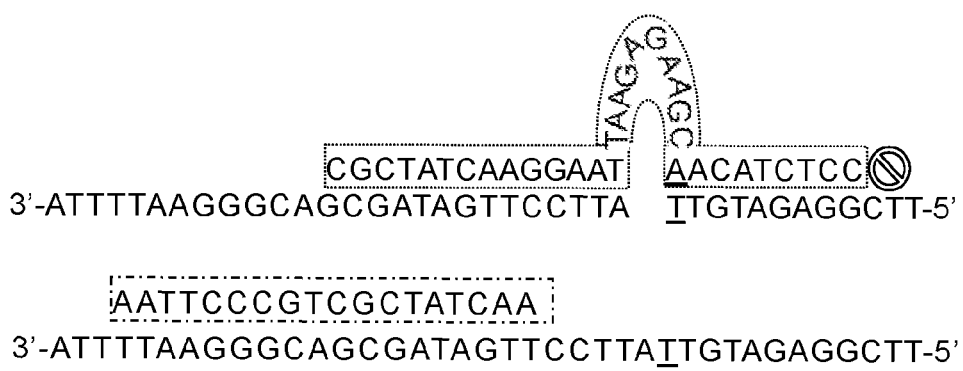
3'-ATTTTAAGGGCAGCGATAGTTCCTTA  TTGTAGAGGCTT-5'

AATTCCCGTCGCTATCAA
3'-ATTTTAAGGGCAGCGATAGTTCCTTATTGTAGAGGCTT-5'

FIG. 1

SEQUENCE LISTING

```
<160> NUMBER OF SEQ ID NOS: 21

<210> SEQ ID NO 1
<211> LENGTH: 10
<212> TYPE: DNA
<213> ORGANISM: Homo sapiens
<220> FEATURE:
<223> OTHER INFORMATION: EPIDERMAL GROWTH FACTOR RECEPTOR EXON 19

<400> SEQUENCE: 1
taagagaagc                                                          10

<210> SEQ ID NO 2
<211> LENGTH: 33
<212> TYPE: DNA
<213> ORGANISM: Artificial Sequence
<220> FEATURE:
<223> OTHER INFORMATION: PRIMER

<400> SEQUENCE: 2
cgctatcaag gaattaagag aagcaacatc tcc                                33

<210> SEQ ID NO 3
<211> LENGTH: 18
<212> TYPE: DNA
<213> ORGANISM: Artificial Sequence
<220> FEATURE:
<223> OTHER INFORMATION: PRIMER

<400> SEQUENCE: 3
aattcccgtc gctatcaa                                                 18

<210> SEQ ID NO 4
<211> LENGTH: 11
<212> TYPE: DNA
<213> ORGANISM: Homo sapiens
<220> FEATURE:
<223> OTHER INFORMATION: ATP13A2 GENE EXON 16

<400> SEQUENCE: 4
cccagagcct c                                                        11

<210> SEQ ID NO 5
<211> LENGTH: 18
<212> TYPE: DNA
<213> ORGANISM: Artificial Sequence
<220> FEATURE:
<223> OTHER INFORMATION: PRIMER
```

```
<400> SEQUENCE: 5
ctggtcccag agcctcgc                                                       18

<210> SEQ ID NO 6
<211> LENGTH: 17
<212> TYPE: DNA
<213> ORGANISM: Artificial Sequence
<220> FEATURE:
<223> OTHER INFORMATION: PRIMER

<400> SEQUENCE: 6
gcattcctgc ccctggt                                                        17

<210> SEQ ID NO 7
<211> LENGTH: 91
<212> TYPE: DNA
<213> ORGANISM: Artificial Sequence
<220> FEATURE:
<223> OTHER INFORMATION: HYPOTHETICAL SELECTED SEQUENCE

<400> SEQUENCE: 7
tgcggcgggt cttactcacc ttttaactta aagagaacta cgggttcacg atggggtcag         60
gataacaaaa atctttgatc tagaatgcac t                                        91

<210> SEQ ID NO 8
<211> LENGTH: 100
<212> TYPE: DNA
<213> ORGANISM: Artificial Sequence
<220> FEATURE:
<223> OTHER INFORMATION: PRIMER

<400> SEQUENCE: 8
gtaacccctt gcggcgggtc ttactcacct tttaacttaa agagaactac gggttcacga         60
tggggtcagg ataacaaaaa tctttgatct agaatgcact                              100

<210> SEQ ID NO 9
<211> LENGTH: 17
<212> TYPE: DNA
<213> ORGANISM: Artificial Sequence
<220> FEATURE:
<223> OTHER INFORMATION: PRIMER

<400> SEQUENCE: 9
aggctagcgt aacccct                                                        17

<210> SEQ ID NO 10
<211> LENGTH: 48
<212> TYPE: DNA
<213> ORGANISM: Homo sapiens
<220> FEATURE:
<223> OTHER INFORMATION: EPIDERMAL GROWTH FACTOR RECEPTOR EXON 19

<400> SEQUENCE: 10
taaaattccc gtcgctatca aggaattaag agaagcaaca tctccgaa                      48

<210> SEQ ID NO 11
<211> LENGTH: 48
<212> TYPE: DNA
<213> ORGANISM: Homo sapiens
<220> FEATURE:
<223> OTHER INFORMATION: EPIDERMAL GROWTH FACTOR RECEPTOR EXON 19

<400> SEQUENCE: 11
ttcggagatg ttgcttctct taattccttg atagcgacgg gaatttta                      48
```

<210> SEQ ID NO 12
<211> LENGTH: 15
<212> TYPE: DNA
<213> ORGANISM: Homo sapiens
<220> FEATURE:
<223> OTHER INFORMATION: EPIDERMAL GROWTH FACTOR RECEPTOR EXON 19 MUTANT

<400> SEQUENCE: 12
ggaattaaga gaagc                                                        15

<210> SEQ ID NO 13
<211> LENGTH: 15
<212> TYPE: DNA
<213> ORGANISM: Homo sapiens
<220> FEATURE:
<223> OTHER INFORMATION: EPIDERMAL GROWTH FACTOR RECEPTOR EXON 19 MUTANT

<400> SEQUENCE: 13
gaattaagag aagca                                                        15

<210> SEQ ID NO 14
<211> LENGTH: 10
<212> TYPE: DNA
<213> ORGANISM: Homo sapiens
<220> FEATURE:
<223> OTHER INFORMATION: EPIDERMAL GROWTH FACTOR RECEPTOR EXON 19 MUTANT

<400> SEQUENCE: 14
ttaagagaac                                                              10

<210> SEQ ID NO 15
<211> LENGTH: 20
<212> TYPE: DNA
<213> ORGANISM: Homo sapiens
<220> FEATURE:
<223> OTHER INFORMATION: EPIDERMAL GROWTH FACTOR RECEPTOR EXON 19 MUTANT

<400> SEQUENCE: 15
aattaagaga agcaacatct                                                   20

<210> SEQ ID NO 16
<211> LENGTH: 15
<212> TYPE: DNA
<213> ORGANISM: Homo sapiens
<220> FEATURE:
<223> OTHER INFORMATION: EPIDERMAL GROWTH FACTOR RECEPTOR EXON 19 MUTANT

<400> SEQUENCE: 16
taagagaagc aacgt                                                        15

<210> SEQ ID NO 17
<211> LENGTH: 227
<212> TYPE: DNA
<213> ORGANISM: Homo sapiens
<220> FEATURE:
<223> OTHER INFORMATION: ATP13A2 GENE EXON 16

<400> SEQUENCE: 17
acgggcaccc tcactgagga cggcttagac gtgatggggg tggtgcccct gaagggggcag      60 gcattcctgc ccctggtccc agagcctcgc cgcctgcctg ggggcccctg ctccgagcac      120
tggccacctg ccatgccctc agccggctcc aggacacccc cgtgggcgac cccatggact      180
tgaagatggt ggagtctact ggctgggtga ggaggccaag caggtca                    227

```
<210> SEQ ID NO 18
<211> LENGTH: 355
<212> TYPE: DNA
<213> ORGANISM: Artificial Sequence
<220> FEATURE:
<223> OTHER INFORMATION: HYPOTHETICAL TARGET SEQUENCE

<400> SEQUENCE: 18
gacccaagag gctagcgtaa ccccttgcgg cgggtcttac tcaccttta acttaaagag      60 aactacgggt tcacgatggg gtcaggataa caaaaatctt tgatctagaa tgcactagta    120
gtctaagagg tgaggtatac cgttagtcag ccgtattgag actgtgcgtc gtctaagagg    180
gtgcagtgga gtagattcag tcgatctagc gaagagaacc ggcatgatcc gatactatac    240
atctacgaca attccattgc tttgtgagag cctttacctt tactcatgga cccgtgctgc    300
tggtagccgc ttatacatat tcatgggttc tcccggattc aaaaacagag gcagg         355

<210> SEQ ID NO 19
<211> LENGTH: 20
<212> TYPE: DNA
<213> ORGANISM: Artificial Sequence
<220> FEATURE:
<223> OTHER INFORMATION: PRIMER

<400> SEQUENCE: 19
agcagctgcc agacatgaga                                                 20

<210> SEQ ID NO 20
<211> LENGTH: 21
<212> TYPE: DNA
<213> ORGANISM: Artificial Sequence
<220> FEATURE:
<223> OTHER INFORMATION: PRIMER

<400> SEQUENCE: 20
gtgaggaggc caagcaggtc a                                               21

<210> SEQ ID NO 21
<211> LENGTH: 21
<212> TYPE: DNA
<213> ORGANISM: Artificial Sequence
<220> FEATURE:
<223> OTHER INFORMATION: PRIMER

<400> SEQUENCE: 21
tgtataagcg gctaccagca g                                               21
```

POLYMERASE CHAIN REACTION-BASED METHOD AND PRIMER SET FOR DETECTING EPIDERMAL GROWTH FACTOR RECEPTOR MUTATION

BACKGROUND OF THE INVENTION

1. Field of the Invention

The present disclosure relates to methods and primer sets for detecting variant(s). More particularly, the disclosed invention relates to the detection of insertion and/or deletion variant(s).

2. Description of Related Art

Gene mutations are alterations in the nucleotide sequence of a given gene or regulatory sequence from a naturally occurring or normal nucleotide sequence. A mutation may be a point mutation (single nucleotide substitution), a deletion, or insertion mutation of one or more nucleotides, a substitution mutation of more than one nucleotide, or crossing-over in chromosomal level.

Various techniques for detecting point mutations or crossing-overs have been developed. For examples, mutated nucleotide(s) could be revealed by Sanger's direct sequencing of sequence of interest. However, the sensitivity of this technique is too low, hindering its application in clinical and research uses. Alternatively, primers and/or probes specific to the target genes with point mutations or crossing-overs could be used to positively detect such mutations. However, there are few reports on detection of an insertion mutation and a deletion mutation using any of the above-mentioned method. Conventionally, primers or probes for detecting an insertion/deletion mutation are designed with prior knowledge of the sequence of the mutated site. In the case where the target gene has more than one inserted and/or deleted nucleotide, multiple primers are required to ensure the full coverage of all mutated sequences. Also, these methods tends to be error-prone, since the hybridization of the primer or probe with the target nucleic acid might occur with a mutation site being looped out, and thus unspecific hybridization occurs. Moreover, these conventional detecting methods usually have lower detection sensitivity, thereby requiring higher amount of DNA and/or more reaction cycles that are labor-intensive. In some cases, real-time quantitative polymerase chain reaction (RTQ-PCR) and/or apparatus for RTQ-PCR are required to accomplish the detection process. Therefore, in order to ensure accurate detection results, conventional methods require optimization of reaction parameters which may be costly, tedious, and/or time-consuming, and these factors limit their applications in clinical tests and basic research.

In view of the foregoing, there exists a need in the art for the development of a detection method capable of accurately detecting insertion and/or deletion mutations.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is based on, at least in part, a novel primer design scheme which allows the amplification and thus detection of a variant, as compared with a reference sequence, of a target gene in a sample. Particularly, the target gene has a template strand and a coding strand complementary to the template strand, and the present primer set and method are directed to a selected region of the coding strand. The selected sequence of interest may include the presence or absence of at least one variant nucleotide that is inserted in and/or deleted from the reference nucleotide sequence. In one example, the reference sequence may be a wild-type (normal) sequence, while the variant may comprise an insertion and/or deletion mutation. Alternatively, the reference sequence may be a known mutated sequence, while a variant thereof may be a wild-type sequence and any other mutated sequence.

In view of the foregoing, a first aspect of the invention pertains to a primer set in accordance with the primer design scheme. It should be noted that, prior knowledge of the sequence that is inserted in or deleted from the reference sequence is not required in designing a primer set in accordance with this scheme. But, of course, the present primer set is also applicable to cases in which the variant sequence is known. Accordingly, a single primer set as taught herein is capable of amplifying various variant sequences located within the selected region. Therefore, in the present disclosure, the process for amplifying these mutations is sometimes referred to as universal insertion/deletion polymerase chain reaction (Unidel-PCR) or "PCR" for short.

According to one embodiment, the primer set for used in the PCR-based method described herein comprises a blocking primer and a forward primer. The blocking primer is designed to prevent the reference sequence from being amplified during the PCR. To this end, the blocking primer comprises a sequence that is identical to the reference sequence of the selected region of the coding strand and at least one nucleotide residue immediately precedes the selected region of the coding strand, and the 3'-end of the blocking primer is modified to prevent the extension of nucleotide during the PCR. The forward primer comprises a sequence identical to the nucleotide residues located upstream of the selected region of the coding strand, and at least the last nucleotide residue of the 3'-end of the forward primer is identical to at least the first nucleotide residue of the 5'-end of the blocking primer.

According to another embodiment, the 3'-end of the blocking primer is modified with a phosphate group, a phosphate ester, an inverted 3'-3' linkage, a 2°,3'-dideoxynucleoside, or a 3'-deoxynucleoside.

In optional embodiment, the melting temperature (Tm) of the forward primer is different from the Tm of the blocking primer. According to some embodiments, both of the blocking primer and the forward primer respectively have a Tm no less than about 50° C. In an optional embodiment, the blocking primer has a Tm of about 65-75° C., whereas the forward primer has a Tm of about 50-60° C. Still optionally, the blocking temperature may have a Tm lower than that of the forward primer.

According to another embodiment, the blocking primer has 10-100 nucleotides in length. According to yet another embodiment, the forward primer has 10-30 nucleotides in length. According to still another embodiment, the last 5-10 nucleotides of the 3'-end of the forward primer is identical to the first 5-10 nucleotides of the 5'-end of the blocking primer.

In one example, the selected region has a sequence of SEQ ID NO. 1, the blocking primer has a sequence of SEQ ID NO. 2, and the forward primer has a sequence of SEQ ID NO. 3. In another example, the selected region has a sequence of SEQ ID NO. 4, the blocking primer has a sequence of SEQ ID NO. 5, and the forward primer has a sequence of SEQ ID NO. 6. In still another example, the selected region has a sequence of SEQ ID NO. 7, the blocking primer has a sequence of SEQ ID NO. 8, and the forward primer has a sequence of SEQ ID NO. 9.

A second aspect of the invention pertains to a PCR-based method for detecting an insertion or deletion variant, as compared with a reference sequence, in a selected region of a target gene in a sample, in which the target gene has a template strand and a coding strand complementary to the template strand. As the experimental results below suggest, the present method exhibited ultra-high sensibility in detecting insertion/deletion variant. Also, the present method is capable of detecting such variant nucleotide(s) with or without prior knowledge of the sequence that is inserted or deleted.

According to one embodiment, the PCR-based method comprises the steps as follows. A sample comprising the target gene is mixed with a primer set according to the above described aspect/embodiments of the present disclosure to obtain a reaction mixture. Then, the mixture is subjected to a PCR condition which comprises, subjecting the reaction mixture sequentially to a denature temperature, an annealing temperature, and an extension temperature. Under the annealing temperature, the forward primer and the blocking primer compete to anneal to the template strand of the target gene. Thereafter, whether a PCR product is obtained through the PCR process is determined. In this embodiment, the presence of the PCR product is indicative of the presence of insertion or deletion variant(s) in the selected region of the target gene in the sample, and the absence of the PCR product is indicative of the absence of insertion or deletion variant (s) in the selected region of the target gene in the sample.

According to another embodiment, the amount of blocking primer to the amount of the forward primer in the mixture is about 1:1 to 10:1 by molar ratio; preferably, 3:1 to 10:1.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 1 is a schematic diagram illustrating the primer design scheme according to the present disclosure.

DESCRIPTION

Figure 2:
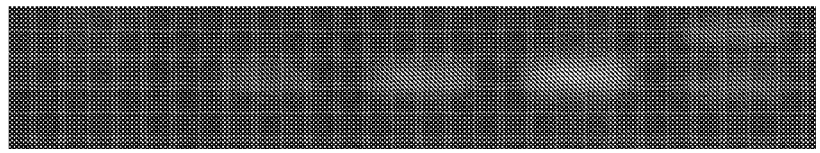
FIG. 2 is a photograph showing the electrophoresis results of detecting the insertion/deletion mutation according to one example of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "nucleotide" refers to a chemical compound that consists of a heterocyclic base, a sugar, and one or more phosphate groups. In the most common nucleotides the base is a derivative of purine or pyrimidine, and the sugar is the pentose deoxyribose or ribose. The purines include adenine (A), and guanine (G); the pyrimidines include cytosine (C), thymine (T), and uracil (U). The term "nucleotide sequence" is used to refer to the ordering of nucleotides in an oligonucleotide or polynucleotide in a single-stranded form of nucleic acid. Unless specified otherwise, the left-hand end of single-stranded nucleotide sequences is the 5' end; and the right-hand end of single-stranded nucleotide sequences is the 3' end. The term "downstream" refers to a nucleotide sequence that is located 3' to a previously mentioned nucleotide sequence. The term "upstream" refers to a nucleotide sequence that is located 5' to a previously mentioned nucleotide sequence.

The term "target gene" as used herein refers to a nucleotide sequence of interest which is investigated for the presence or absence of insertion/deletion variant(s) in a "selected region" thereof. Generally, the target gene is in the form of a double-strand DNA, which consists of a template strand and a coding strand that is complementary to the template strand. According to common practice, the sequence of the coding strand is oriented in the 5' to 3' direction, whereas the sequence of the template strand is oriented in the 3' to 5' direction. According to aspects/embodiments of the present disclosure, the blocking primer and forward primer are designed to hybridize (or anneal) with a specified sequence of the template strand.

The term "reference sequence" is used herein to describe a sequence having a specific sequence of interest. The reference sequence may be a "wild-type" (or "non-mutated", or "normal") sequence that has no insertion/deletion mutation in the selected region thereof. Alternatively, the reference sequence may be a mutated sequence.

As used herein, the term "variant" refers to a change of one or more nucleotide of a reference sequence. In the case where the reference sequence is a wild-type sequence, the variant sequence may be any mutated sequence that has an insertion mutation and/or a deletion mutation. In the case where the reference sequence is a known mutated sequence, the variant sequence includes the wild-type sequence as well as other mutated sequences.

The term "insertion variant" as used herein is directed to a variant identified by the presence of one or more additional nucleotide in the reference nucleic acid molecule, and hence, an insertion variant includes insertion mutations. Also, a gene splicing sequence in which additional bases are added into the DNA strand is considered to fall within the scope of insertion mutations. The term "deletion variant" relates to a variant generated by removal of one or more nucleotide from the reference nucleic acid molecule, and includes deletion mutations. The terms "insertion and/or deletion variant" and "insertion/deletion variant" are used interchangeably herein to refer to a variant that is either an insertion variant or a deletion variant or a combination of both. For example, a crossing-over sequence is considered to comprise both an insertion mutation and a deletion mutation.

The term "forward primer" as used herein refers to a single stranded nucleotide sequence which is complementary to a nucleic acid strand to be copied. The forward primer is capable of acting as a point of initiation of synthesis of a primer extension product, when placed under suitable conditions (e.g., buffer, salt, temperature, and pH) in the presence of nucleotides and an agent for nucleic acid polymerization (e.g., a DNA-dependent or RNA-dependent polymerase). In particular, the "forward primer" hybridizes (or anneals) with the sequence complementary to the 5'-end of the coding strand. As used herein, a "blocking primer" is a single stranded nucleotide sequence that hybridizes (or anneals) with at least the sequence complementary to the 5'-end of the selected region, and as its name suggests, the blocking primer would not initiate the amplification of the nucleotide sequence to which it hybridizes.

The term "hybridization" refers to the formation of complexes between nucleotide sequences which are sufficiently complementary to form complexes (or hybrids) via Watson-Crick base pairing or non-canonical base pairing. The hybridization may take place between two DNA strands, two RNA strands, or one DNA and one RNA strand. The hybridization occurs under a variety appropriate conditions (e.g. temperature, pH, salt concentration, etc.) that are well known in the art of molecular biology.

As used herein, the term "amplification" refers to a method or process that increases the representation of a population of specific nucleotide sequences in a sample. Polymerase chain reaction or PCR is a well-known amplification process in the art and is discussed in more detail below. As used herein, the terms "reaction mixture" and "mixture" are used interchangeably to refer to components that are subjected to a polymerase chain reaction.

The primer design scheme is now discussed with reference to FIG. 1 to facilitate understanding of the present disclosure. It should be noted that sequences depicted in FIG. 1 are provided for the purpose of discussion and as examples, and thus, the claims that follow should not be limited in any way by these sequences.

As illustrated in FIG. 1, the target gene is epidermal growth factor receptor (EGFR) exon 19, the coding strand comprises the $2214^{th}$ to $2261^{st}$ nucleotides of EGFR exon 19 and has a sequence of TAAAATTCCCGTCGCTAT-CAAGGAATTAAGAGAAGCAACATCTCCGAA (SEQ ID NO. 10), and a template strand complementary to the coding strand has a sequence of 3'-ATTTTAAGGGCAGC-GATAGTTCCTTAATTCTCTTCGTTGTAGAGGCTT-5' (SEQ ID NO. 11). In the context of present disclosure, the coding strand has a selected region which is under investigation for the presence or absence of insertion/deletion mutation(s) in this selected region. In the present example, the reference sequence of the selected region within the coding strand is TAAGAGAAGC (SEQ ID NO. 1, which are the $2240^{th}$ to $2249^{th}$ nucleotides of wild-type EGFR exon 19, indicated by underlined in FIG. 1).

Theoretically, the selected region to be investigated could have any number of nucleotides. According to optional embodiments of the present invention, the selected region may have about 99 nucleotides at maximum. For example, the length of the selected region may be about 5, 10, 15, 20, 25, 30, 35, 40, 45, 50, 55, 60, 65, 70, 75, 80, 85, 90, 95, or 99 nucleotides.

In order to provide a method for detecting the insertion/deletion variant in the selected region, two primers (i.e., blocking primer and forward primer) that respectively bind to different but overlapping portions of the template strands are designed. Detailed information regarding these two primers is provided hereinbelow.

Blocking Primer

The present blocking primer comprises a sequence that is identical to the reference sequence of the selected region of the coding strand and at least one nucleotide residue that immediately precedes the selected region of the coding strand such that it may hybridize with the complement of the selected region and at least one adjacent nucleotide under appropriate hybridization conditions. Optionally, the blocking primer further comprises at least 5 to 20 consecutive nucleotide residues immediately preceding the selected region. Still optionally, the blocking primer may further comprise at least one nucleotide residue immediately succeeding the selected region of the coding strand. Still optionally, the nucleotide residues immediately succeeding the selected region may be at least 5 to 20 nucleotide residues. For example, as depicted in FIG. 1, one exemplified blocking primer has the sequence of CGCTAT-CAAGGAATTAAGAGAAGCAACATCTCC (SEQ ID NO. 2, the selected region is italicized). As illustrated in FIG. 1, this blocking primer includes 15 consecutive nucleotide residues (CGCTATCAAGGAAT) immediately preceding the selected region and 9 consecutive nucleotide residues (AACATCTCC) immediately succeeding the selected region. As could be appreciated by persons with ordinary skills in the art, a more stable hybrid is formed when there is no insertion/deletion mutation within the selected sequence since the blocking primer covers the full stretch of the selected region. By contrast, when the inserted/deleted nucleotide locates within the selected sequence, the misalignment between the blocking primer and the template strand would create a loop in wither the blocking primer or the template strand thereby forming a less stable hybrid (see, FIG. 1). Alternatively, when the inserted/deleted nucleotide locates at the start or end of the selected sequence, the mismatch between the blocking primer and template strand would create a fork at either end thereby forming a less stable hybrid (not shown).

As its name suggests, the blocking primer is modified to block the extension of the blocking primer during PCR. This may be achieved by modifying the 3'-terminus of a normal primer with a non-nucleosidic blocker, such as a phosphate group, or a phosphate ester. For example, the 3'-propyl phosphate formed using 3'-Spacer C3 cytosine-phosphate-guanine (CPG) is one of the effective non-nucleosidic blocker of the 3'-terminus. Having a single inverted base at the 3' position with a 3'-3' linkage also prevents nucleotide extension by polymerases as there is no free 3' hydroxyl group to initiate synthesis. Another way to avoid polymerase extension at the 3' terminus is using a nucleosidic blocker such as a 2',3'-dideoxynucleoside (e.g., 2',3'-ddC-CPG) or a 3'-deoxynucleoside (e.g., 3'-dA-CPG, 3'-dC-CPG, 3'-dG-CPG, or 3'-dT-CPG). These and other equivalent techniques for modifying the 3' end of the blocking primer are envisioned and all should be considered to be within the scope of the present disclosure.

According to the principles and spirits of the present disclosure, the blocking primer shall cover the full stretch of the selected region and at least one additional nucleotide residue. Therefore, the present blocking primer shall have about at least 10-100 nucleotides in length according to some embodiments of the present disclosure. As could be appreciated by persons with ordinary skill in the art, the exact length of the blocking primer depends on the length of the selected region of interest, as well as on the conditions at which the primer is used, such as the annealing temperature and ionic strength. For example, the blocking primer as depicted in FIG. 1 has 33 nucleotide residues.

According to some embodiments of the present invention, the melting temperature of the blocking primer is no less than about 50° C. Optionally and more preferably, the Tm of the blocking primer is between about 55-85; and more preferably, between about 65-75° C. Specifically, the Tm of the blocking primer may be about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85° C. The Tm of the blocking primer of SEQ ID NO. 2 is about 69° C.

Forward Primer

The present forward primer is designed to have its 3'-end overlapped with the 5'-end of the blocking primer. In this way, the blocking primer and the forward primer, under hybridizing conditions, may compete for the overlapping nucleotide residue(s) in order to hybridize with the complement of the coding strand (i.e., the template strand). Specifically, the forward primer comprises a sequence identical to the nucleotide residues located upstream of the selected region, and at least the last nucleotide residue of the 3'-end of the forward primer is identical to at least the first nucleotide residue of the 5'-end of the blocking primer. Optionally, at least the last 5, 10, or 15 consecutive nucleotide residues of the forward primer, is identical to at least the first 5, 10, or 15 consecutive nucleotide residues of the blocking primer. The exemplified forward primer as depicted in FIG. 1 has the sequence of AATTCCCGTCGC-TATCAA (SEQ ID NO. 3), in which the last 9 consecutive residues (CGCTATCAA) are identical to the first 9 consecutive residues of the blocking primer.

According to some embodiments, the forward primer has 10-30 nucleotides in length. According to the principles and spirits of the present disclosure, the exact length of the forward primer depends on the desired overlapping nucleotide residue(s) with the blocking primer, as well as on conditions at which the primer is used, such as the annealing temperature and ionic strength. For example, the forward primer as depicted in FIG. 1 has 18 nucleotide residues.

According to some embodiments of the present invention, the melting temperature of the forward primer is no less than about 50° C. Optionally and more preferably, the Tm of the forward primer is between about 50-70° C.; and more preferably, between about 55-60° C. Specifically, the Tm of the blocking primer may be about 50, 51, 52, 53, 54, 55, 56, 57, 58, 59, 60, 61, 62, 63, 64, 65, 66, 67, 68, 69, or 70° C. The Tm of the forward primer of SEQ ID NO. 3 is about 55° C.

It should be noted that, in optional embodiments, the melting temperature of the blocking primer is different from that of the forward primer. In this way, it is possible to control the respective hybridization of the two respective primers to the template strand by subjecting the PCR reaction mixture containing these two primers under different annealing temperatures. Generally, the melting temperature of the blocking primer may be 5, 6, 7, 8, 9, 10, 11, 12, 13, 14, or 15° C. different from that of the forward primer. In the example illustrated in FIG. 1, the Tm difference between the two primers is about 14° C.

Method for Detecting Insertion/Deletion Variant

Now that the present primer design scheme and an exemplary primer set have been discussed in detail, attention is directed to the PCR-based detection method using such primer set.

According to one embodiment, a sample containing the target gent is mixed with a present primer set to obtain a mixture for use in subsequent PCR process. The target gene is a double stranded DNA having a template strand and a coding strand complementary to the template strand.

It could be appreciated that the primer set for use in the present method is designed in accordance with the scheme discussed hereinabove, and thus detailed descriptions regarding the blocking primer and forward primer are omitted herein for the sake of brevity and clarity.

According to various embodiments, the blocking primer and the forward primer are present in the mixture in a molar ratio of about 1:1 to 10:1; and preferably about 3:1 to 10:1. For example, the molar ratio may be about 1:1, 1:2, 1:3, 1:4, 1:5, 1:6, 1:7, 1:8, 1:9, or 1:10. In one working example, about 0.2 μM forward primer and about 1 μM blocking primer are present in the reaction mixture.

Generally, the template strand (and thus, the coding strand) may or may not have insertion/deletion variant(s) in relative to the reference sequence within the selected region. According to the principles and spirits of the present disclosure, the present method is applicable in situations where the variant sequence is known or unknown.

In some circumstances, a biological sample subjected to detection by the present method may contain both the wild-type sequence and the mutated sequence. For example, in a sample harboring from the tissue of an organism, some mutated cells might exist therein. In this case, the amount of the mutated sequence only accounts for a minor fraction in relation to the wild-type sequence. Since the present method exhibits ultra-high sensibility in detecting insertion/deletion mutation, the scarcity of the mutated sequence will not post any difficulty in detection. In one example, in a sample containing both the wild-type and mutated sequences, the present method is capable of detecting the mutated sequence even when the amount of mutated sequence is only 1/10,000 of the amount of the wild-type sequence. Furthermore, according to some examples, only 10-1000 copies of the target gene are sufficient for detection.

As could be appreciated by persons with ordinary skills in the art, the reaction mixture may further comprise other amplification reaction reagents. These amplification reaction reagents are used in PCR and may include, but are not limited to, buffers, reagents, enzymes having reverse transcriptase and/or polymerase activity or exonuclease activity;

enzyme cofactors such as magnesium or manganese; salts; and deoxynucleotide triphosphates (dNTPs) such as deoxyadenosine triphosphate (dATP), deoxyguanosine triphosphate (dGTP), deoxycytidine triphosphate (dCTP), deoxythymidine triphosphate (dTTP) and deoxyuridine triphosphate (dUTP). Amplification reaction reagents may readily be selected by one skilled in the art depending on the PCR process used.

The reaction mixture is then subjected to a modified PCR process. In particular, the modified PCR process comprises, sequentially in steps, a denaturing step, an annealing step, and an extension step.

In the denaturing stage, the DNA duplex formed by the template strand and the coding strand are denatured (i.e., melted). The precise denaturing behavior of the DNA duplex is unique to its size, sequence, and molecular composition (primarily, the ratio of guanine-cytosine bonds to adenine-thymine bonds, or G-C %). The denaturing of DNA duplex occurs in less than one second, at temperatures from about 80° C. or lower (for small targets with a low G-C %) to about 95° C. (for human genomic DNA).

After the denaturing stage, the reaction mixture is cooled to an annealing temperature so that the blocking primer and the forward primer compete to anneal to the template strand It would be appreciated by any skilled artisan that the hybridizing sequences need not have perfect complementarity. Therefore, the blocking primer may hybridize with the template strand of the reference sequence as well as with the template strand having insertion/deletion variant within the selected region. However, as discussed above, the hybrid formed between the blocking primer and the variant template strand would be less stable in relative to the hybrid formed between the blocking primer and the reference template strand, and thus the hybrid of the blocking primer and the variant template strand tends to denature thereby allowing the forward primer to anneal with such variant template strand to form a relatively stable hybrid. Therefore, the target gene having variant nucleotide(s) in the selected region may be amplified during the subsequent extension step, whereas the target gene having a reference sequence that anneals with the blocking primer would not be amplified during the subsequent extension step.

In an optional embodiment, the annealing step comprises two stages. At the first annealing stage, the first annealing temperature is lower than the Tm of the blocking primer but higher than the Tm of the forward primer. In this instance, only the blocking primer would hybridize with the template strand, whereas the forward primer would not hybridize with the template strand. Thereafter, in the second annealing stage, the mixture is further cooled to the second annealing temperature, which is lower than the Tm of the forward primer, thereby allowing the forward primer to hybridize with the template strand. However, the forward primer is specifically designed to have its 3'-end overlaps the 5'-end of the blocking primer. Therefore, in the case where the blocking primer has already formed a relatively stable hybrid with the template strand in the first annealing stage, the hybrid formed by the forward primer and the template strand would become relatively unstable due to the fork structure created at the 3'-end of the forward primer (see, FIG. 1). In other words, for a reference coding strand that has no insertion/deletion mutation in the selected region, the blocking primer would stably anneal to the reference template strand and therefore inhibit the extension of nucleotides during the subsequent stage. On the other hand, in the situation where the blocking primer has formed a relatively unstable hybrid with the template strand due to the variant nucleotide(s) present in the selected region, said hybrid tends to denature thereby allowing the forward primer to anneal with such variant template strand to form a relatively stable hybrid. Therefore, the target gene having variant nucleotide(s) in the selected region may be amplified during the subsequent extension step, whereas the target gene having a reference sequence that anneals with the blocking primer would not be amplified during the subsequent extension step.

After the annealing step, the mixture is subjected to the extension temperature which allows the extension of nucleotides. Optimal extension temperatures are well-known in the prior art. Generally, the extension temperature is between about 70-80° C. However, other temperatures may be used depending on factors such as the polymerase that are used.

The reaction mixture is then cycled through the denaturing, annealing, and extension steps to allow the amplification of the target gene; in particular, the target gene having variant nucleotide(s) in the selected region thereof. The present modified PCR process may be carried out in any known PCR thermocycler and equivalents thereof. Further, the present PCR-based method is compatible with most of the conventional PCR procedures. Therefore, it is possible to adapt the present method for various PCR techniques, which include but are not limited to asymmetric PCR, hot start PCR, miniprimer PCR, multiplex-PCR, nested PCR, real-time quantitative PCR, reverse transcription PCR, solid phase PCR, and touchdown PCR.

The present method also comprises the detection of the PCR product. According to the present embodiment, the presence of the PCR product is indicative of the presence of insertion/deletion variant (s) in the selected region of the target gene, whereas the absence of the PCR product is indicative of the absence of insertion/deletion variant (s) in the selected region of the target gene.

There are various measures known in the art for determining the presence/absence of a PCR product; these measures include but are not limited to, gel electrophoresis, fluorescence resonant energy transfer, and hybridization to a labeled probe. The probe might be labeled with biotin, at least one fluorescent moiety, an antigen, a molecular weight tag, and a modifier of probe Tm. The detection step might also comprise the incorporation of a label (e.g., fluorescent or radioactive) during the extension stage. The detecting step comprises measuring fluorescence, mass, charge, and/or chemiluminescence. The detection step may be performed during the course of the PCR process (e.g., in a real-time PCR process) or upon the completion of the PCR process.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

Example I

Detection of Insertion/Deletion Mutation in EGFR Exon 19

A total of 134 clinical samples were collected from patients in Mackay Memorial Hospital (Taiwan) with informed consent. Samples were processes to isolate nucleic acid. In an initial experiment, the Unidel-PCR amplification was performed using the following ingredients, PCR Buffer2× Master mix (JMR) 20 µl, 0.2 µM forward primer (SEQ ID NO. 3), 2 µM blocking primer (SEQ ID NO. 2), 0.2 µM reverse primer (AGCAGCTGCCAGACATGAGA, SEQ ID NO. 19), isolated DNA (wild-type or mutated) 1 µl ($10^5$ copies) or template DNA 100 ng, and water to final volume of 20 µl. The cycling condition used in the reaction were, denaturing at 95° C. for 10 min, followed by 45 cycles of 94° C. for 60 sec, 60° C. for 60 sec, 72° C. for 60 sec, and final extension at 72° C. for 10 minutes on ABI 9700 PCR machine.

After the completion of the PCR reaction, a sample was taken from the PCR pouch and electrophoresis was performed on an agarose gel, along with the tube control. The gels were imaged using fluorescence detection with ethidium bromide (EtBr) and a CCD camera detector. Product bands shown on the gel were excised, and the nucleic acids contained therein were sequenced. The sequencing results indicated that several mutated variants of the EGFR exon 19 were detected by the present Unidel-PCR process; the mutated sequences of theses variants, positions thereof and amino acid residues being affected by the mutation are summarized in Table 1. The wild type EGFR exon 19 comprises the sequence of SEQ ID NO. 10, which are the $2214^{th}$ to $2261^{st}$ nucleotides of EGFR exon 19.

TABLE 1

| SEQ ID NO. | Nucleotide number | Sequence | Mutation type | Amino acid sequence |
|---|---|---|---|---|
| 12 | 2235-2249 | GGAATTAAGAGAAGC | Deletion | E746-A750 |
| 13 | 2236-2250 | GAATTAAGAGAAGCA | Deletion | E746-A750 |
| 14 | 2239-2247 | TTAAGAGAAC | Deletion 2248G > C | L747-P749, A750P |
| 15 | 2237-2256 | AATTAAGAGAAGCAACA*TCT* | Deletion Insertion:*TC* | E746-5752 > V |
| 16 | 2240-2254 | TAAGAGAAGCAACGT | Deletion | L747-T751 |

Cross comparison between the sequencing results and the Unidel-PCR results revealed that, for samples containing insertion/deletion mutation, mutated sequences were positively identified in 34 out of 34 samples (Table 2).

TABLE 2

| | | Result of Unidel-PCR | | |
|---|---|---|---|---|
| | | Negative | Positive | Total |
| Result of exon 19 mutation by sequencing | Positive | 0 | 34 | 34 |
| | Negative | 68 | 32 | 100 |
| | Total | 68 | 66 | 134 |

Example II

Detection Sensibility

The sample having mutated DNA fragment of SEQ ID NO. 12 (E746-A750del) was picked to elucidate the sensibility of the present Unidel-PCR. The wild-type DNA fragment and said mutant DNA fragment were serially diluted from $10^7$ copies and mixed in various ratios. The Unidel-PCR amplification was carried out as described in Example I. The PCR products were detected as according to procedures described in Example I, and the results are presented in FIG. 2.

In some experiments, the wild-type DNA fragment and the mutant DNA fragment were present in 100:1 or 10:1 in the reaction mixture for Unidel-PCR. The photograph in FIG. 2 indicates that the wild-type DNA fragment was not amplified during the reaction (Negative control, N), whereas the mutant DNA fragment was amplified (Positive control, P).

Example III

Exemplary Primer Sets

Other exemplary primer sets, which are designed based on similar design scheme of the primer sets of the present disclosure and are suitable for use in the present Unidel-PCR detection method, are provided herein.

ATP13A2 gene encodes the ATPase 13A2 in human; exon 16 of ATP13A2 gene has a sequence of:

```
                                       (SEQ ID NO. 17)
ACGGGCACCCTCACTGAGGACGGCTTAGACGTGATGGGGGT
G   G   T   G   C   C   C   C   T

GAAGGGGCAGGCATTCCTGCCCCTGGTCCCAGAGCCTCGCCG
C   C   T   G   C   C   T   G

GGGGCCCCTGCTCCGAGCACTGGCCACCTGCCATGCCCTCAG
C   C   G   G   C   T   C   C

AGGACACCCCCGTGGGCGACCCCATGGACTTGAAGATGGTG
G   A   G   T   C   T   A   C   T

GGCTGGGTGAGGAGGCCAAGCAGGTCA.
```

To investigate the presence or absence of any insertion/deletion mutation in the selected region of CCCAGAGCCTC (nucleotides 78-88), one exemplary blocking primer may have the sequence of CTGGTCCCAGAGCCTCGC (SEQ ID NO. 5, in which sequence identical to the selected region is bold and italicized), and one forward primer may have the sequence of GCATTCCTGCCCCTGGT (SEQ ID NO. 6) in which the last 5 nucleotide residues of the forward primer overlaps the first 5 nucleotide residues of the blocking primer. The reverse primer has a sequence of GTGAGGAGGCCAAGCAGGTCA (SEQ ID NO. 20).

Another example is directed to an artificial reference sequence having a coding strand of:

```
                                       (SEQ ID NO. 18)
GACCCAAGAGGCTAGCGTAACCCCTTGCGGCGGGTCTTACTC
A   C   C   T   T   T   T   A

ACTTAAAGAGAACTACGGGTTCACGATGGGGTCAGGATAACAA
A   A   A   T   C   T   T

TGATCTAGAATGCACTAGTAGTCTAAGAGGTGAGGTATACCG
T   T   A   G   T   C   A   G

CCGTATTGAGACTGTGCGTCGTCTAAGAGGGTGCAGTGGAGT
A   G   A   T   T   C   A   G

TCGATCTAGCGAAGAACCGGCATGATCCGATACTATACAT
C   T   A   C   G   A   C   A

ATTCCATTGCTTTGTGAGAGCCTTTACCTTTACTCATGGACCC
G   T   G   C   T   G   C
```

-continued

TGGTAGCCGCTTATACATATTCATGGGTTCTCCCGGATTCAA
 A   A   A   C   A   G   A   G

GCAGG.

To investigate the presence or absence of any insertion/deletion variant in the selected region thereof (nucleotides 25-116), one exemplary blocking primer may have the sequence of GTAACCCCTTGCGGCGGGTCTTACTCAC-CTTTTAACTTAAAGAGAACTACGGG TTCAC-GATGGGGTCAGGATAACAAAAATCTTTGATCTA-GAATGCACT (SEQ ID NO. 8, in which sequence identical to the selected region is bold and italicized), and one forward primer may have the sequence of AGGCTAGCGTAAC-CCCT (SEQ ID NO. 9) in which the last 9 nucleotide residues of the forward primer overlaps the first 9 nucleotide residues of the blocking primer. The reverse primer has a sequence of TGTATAAGCGGCTACCAGCAG (SEQ ID NO. 21).

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A polymerase chain reaction (PCR)-based method for detecting an insertion or deletion variant, as compared with a reference sequence, in a selected region of a target gene in a sample, wherein the selected region has the sequence of SEQ ID NO. 1, the method comprising the steps of,
   (a) forming a mixture comprising the sample and a primer set, wherein the target gene in the sample comprises a template strand and a coding strand complementary to the template strand, and the primer set comprises,
      (i) a blocking primer having the sequence of SEQ ID NO. 2; and
      (ii) a forward primer having the sequence of SEQ ID NO. 3;
   (b) subjecting the mixture to, sequentially in steps, a denaturing step, an annealing step, and an extension step, wherein in the annealing step the forward primer and the blocking primer compete to anneal to the template strand; and
   (c) determining whether a PCR product is obtained through steps (a) and (b), wherein the presence of the PCR product is indicative of the presence of the insertion or deletion variant in the selected region of the target gene in the sample, and the absence of the PCR product is indicative of the absence of the insertion or deletion variant in the selected region of the target gene in the sample.

2. The method of claim 1, wherein the blocking primer and the forward primer are mixed in a molar ratio from about 1:1 to 10:1 in the mixture.

3. A primer set for detecting an insertion or deletion variant, as compared with a reference sequence, in a selected region of a target gene having a template strand and a complementary coding strand using PCR, wherein the selected region has the sequence of SEQ ID NO. 1, the primer set comprising,
 (i) a blocking primer having the sequence of SEQ ID NO. 2; and
 (ii) a forward primer having the sequence of SEQ ID NO. 3.

4. The primer set of claim 3, wherein the 3'-end of the blocking primer is modified with a phosphate group, a phosphate ester, an inverted 3'-3' linkage, a 2',3'-dideoxynucleoside, or a 3'-deoxynucleoside.

* * * * *